United States Patent [19]

Duembgen et al.

[11] Patent Number: 4,496,770

[45] Date of Patent: Jan. 29, 1985

[54] PROCESS FOR THE PREPARATION OF α-ALKYLACROLEINS

[75] Inventors: Gerd Duembgen, Dannstadt-Schauernheim; Gerd Fouquet, Neustadt; Richard Krabetz, Kirchheim; Ekhart Lucas, Wachenheim; Franz Merger, Frankenthal; Friedbert Nees, Stutensee, all of Fed. Rep. of Germany

[73] Assignee: BASF Aktiengesellschaft, Ludwigshafen, Fed. Rep. of Germany

[21] Appl. No.: 479,475

[22] Filed: Mar. 28, 1983

[30] Foreign Application Priority Data

Apr. 14, 1982 [DE] Fed. Rep. of Germany ......... 3213681

[51] Int. Cl.$^3$ ............................................. C07C 47/22
[52] U.S. Cl. ..................................... 568/463; 568/461
[58] Field of Search ........................... 568/461, 463

[56] References Cited

U.S. PATENT DOCUMENTS

| 2,848,499 | 8/1958 | MacLean et al. | 568/461 |
| 4,317,945 | 3/1982 | Bernhagen et al. | 568/461 |
| 4,346,239 | 8/1982 | Bach et al. | 568/461 |
| 4,408,079 | 10/1983 | Merger et al. | 568/451 |

FOREIGN PATENT DOCUMENTS

| 58927 | 9/1982 | European Pat. Off. | 568/461 |
| 2037767 | 7/1980 | United Kingdom | 568/461 |
| 2038826 | 7/1980 | United Kingdom | 568/461 |
| 2078748 | 1/1982 | United Kingdom | 568/461 |

*Primary Examiner*—Werren B. Lone
*Attorney, Agent, or Firm*—John H. Shurtleff

[57] ABSTRACT

α-Alkylacroleins are prepared by a process wherein an alkanal is reacted with formaldehyde in the presence of a secondary amine and in the presence or absence, of an acid, in the liquid phase, under superatmospheric pressure and at above 150° C., for not more than 25 minutes.

The α-alkylacroleins obtainable by the process are useful starting materials for dyes, drugs and pesticides.

10 Claims, No Drawings

PROCESS FOR THE PREPARATION OF α-ALKYLACROLEINS

The present invention relates to a process for the preparation of α-alkylacroleins by reacting an alkanal with formaldehyde in the presence of a secondary amine and, if desired, of an acid, in the liquid phase, under superatmospheric pressure and at above 150° C., for not more than 25 minutes.

It has been disclosed that α-alkylacroleins can be prepared by Mannich condensation of an n-alkanal with formaldehyde in the presence of a secondary amine:

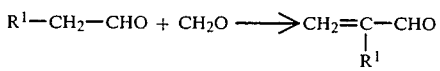

$$R^1-CH_2-CHO + CH_2O \longrightarrow CH_2=\underset{R^1}{C}-CHO$$

In general, the reaction is carried out at above 40° C., under a pressure of 1–10 bar and at a pH>3. In this reaction, the alkanal condenses with formaldehyde in the presence of a secondary amine.

Thus, methacrolein and 2-ethylacrolein can be prepared from propionaldehyde and n-butyraldehyde respectively, and formaldehyde, by the process described in German Patent No. 875,194. In the examples, monocarboxylic acids, e.g. butyric acid and stearic acid, are employed, the molar ratio of propionaldehyde to formaldehyde is 1:1.02, that of propionaldehyde to the secondary amine is 1:0.038, that of propionaldehyde to the acid is 1:0.013 and that of the secondary amine to the acid is 3:1, the residence times are from 4 to 6 hours and the boiling points are as high as 100° C. The reaction is carried out in general at a pH>7.

In a similar process (Germain Laid-Open application DOS No. 2,855,504 and GB No. 2,037,767A) for the preparation of methacrolein, carboxylic acids, e.g. formic acid, acetic acid and in particular propionic acid, and, as secondary amines, dipropylamine, methylbutylamine, ethylbutylamine and in particular di-n-butylamine are singled out. In the example, a yield of 81.7% is achieved in a reaction carried out at 30°–100° C. and under 2.5 bar in the course of 120 minutes. The temperature is stated as being from 70° to 120° C., preferably from 95° to 110° C., the pressure as being from 2 to 10, preferably from 2 to 4, bar, and the residence time as being from 30 to 120 minutes. The stated molar ratios are propionaldehyde:formaldehyde=1:1–1.5, propionaldehyde:secondary amine=1:0.02–0.05 (1:0.025) and propionaldehyde:acid=1:0.01–0.02 (1:0.015). German Laid-Open application DOS No. 3,025,350 (Bach et al, U.S. Pat. No. 4,346,239) also describes a similar reaction, with similar residence times, temperatures and pressures.

In each of the 3 publications, the process described employs a catalytic amount of an amine in conjunction with a carboxylic acid. Obviously, a pH above 7 is essential in order that an adequate reaction velocity can still be achieved at the low catalyst concentration employed, or in order to avoid still higher residence times and hence increased dimerization of the α-alkylacrolein. The disadvantage is that, under the stated conditions, experience has shown that substantial amounts of other aldol condensates are also formed, as is also evident from the example of German Laid-Open application DOS No. 2,855,504 (GB No. 2,037,767A).

U.S. Pat. No. 2,518,416 describes the condensation of an alkanal with formaldehyde in a molten salt RRNH.HX (HX is an acid with an acidity not less than that of trichloroacetic acid), preferably in $(CH_3)_2NH.HCl$, at from 120° to 300° C., preferably from 140° to 220° C., under atmospheric or reduced pressure. In Example 1, a yield of 51% of α-ethylacrolein is obtained from n-butyraldehyde and formaldehyde at from 200° to 220° C., using a molar ratio of salt to aldehyde of 7:1. The large amount of amine salt gives rise to substantial material costs and disposal problems when the materials are not recycled, while recycling entails an expensive processing procedure.

U.S. Pat. No. 2,639,295 describes the condensation of propionaldehyde with formaldehyde in the ratio 2–6:1 (the former being employed in excess), in the presence of not more than 0.25 equivalent of RRNH.HX (where RRNH is a secondary amine and HX is, in particular HCl, HBr, $H_2SO_4$ or $H_3PO_4$), in general at from 80° to 130° C. and at pH 4–6 The excess propionaldehyde is distilled off. The highest reaction temperature given in the examples is 115° C. The optimum yield (Example 8) of 92.5%, based on formaldehyde, is achieved using 5 moles of propionaldehyde per mole of formaldehyde and a 10% strength solution of piperidine .HCl in acetic acid. The reaction is carried out in general in a column (examples). As shown in the examples, the reaction is carried out by a procedure in which the starting materials on the one hand and the boiling catalyst solution on the other hand are fed in countercurrent to one another. The space/time yield (Example 8) is unsatisfactory. The excess of propionaldehydes results in an uneconomical procedure owing to the large amount of material recycled, and the higher selectivity in respect of formaldehyde is achieved at the expense of unavoidable losses of propionaldehyde, inter alia as a result of condensation to methylpentenal. The proposed regeneration of the catalyst by heating at 150°–300° C. is ineffective because the inactive tertiary amine $RRNCH_3$ is formed.

A similar process, but one which comprises two stages, is described in U.S. Pat. No. 2,848,499. In this process, continuous condensation of propionaldehyde/-formaldehyde/RRNH.HX in the ratio of 1:1.2–5 is carried out at 105°–120° C. under superatmospheric pressure. HCl, $H_2SO_4$, $H_3PO_4$ and acetic acid are mentioned as acids. The only example given employs HCl, and shows that, using a ratio of propionaldehyde:formaldehyde:$(CH_3)_2NH.HCl$ of 1:1.036:2.5 at 111° C., a conversion of 98.1% of propionaldehyde and a selectivity of 99.6%, based on propionaldehyde, or 99%, based on formaldehyde, are achieved. In the example, the total residence time in the two stages is not less than 45 minutes. In the process, the amine salt is employed in a large excess, and this has the disadvantages stated above in the connection with U.S. Pat. No. 2,518,416.

Russ. Chem. Rev. 33 (1964), 314 describes the reaction of propionaldehyde, formaldehyde and $(C_2H_5)_2NH.HCL$ in equimolar amounts of pH 6–7 in the course of 20 minutes at 45° C., and the subsequent liberation of the methacrolein.

This two-stage procedure is said to give high selectivities. A pronounced pH-dependence was found: in contrast to pH 3–4, where the reaction had to be carried out at 100°–120° C., at the optimum pH of 6–7 the reaction could be carried out at such a low temperature that high selectivities were achieved without losses due to polymerization. It is found in particular that, in contrast, prior processes are far removed from the optimum. Variable yields which are difficult to reproduce or are unsatisfactory are obtained in this manner. The authors therefore emphasize the importance of the conditions.

All of the above processes are unsatisfactory because none of them combines optimum yield, optimum amount of catalyst and optimum space/time yield and is technically simple to carry out; the processes of German Pat. No. 875,194 and German Laid-Open application DOS No. 2,855,504 do not proceed sufficiently selectively and rapidly, while those of U.S. Pat. Nos. 2,518,416, 2,639,295 and 2,848,499 are technically very complicated (individual components employed in large excess, more difficult conditions) or likewise give poor results; although the process described in Russ. Chem. Rev. (loc. cit.) gives satisfactory yields, it requires a large amount of catalyst and is hence disadvantageous.

We have found that α-alkylacroleins of the formula

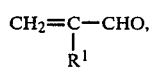  (I)

where $R^1$ is an aliphatic radical, are advantageously obtained by reacting an alkanal of the formula $$R^1-CH_2-CHO \quad (II),$$

where $R^1$ has the above meanings, with formaldehyde in the presence of a secondary amine and, if desired, of an acid, at from 150° to 300° C., if the reaction is carried out in the liquid phase under superatmospheric pressure at above 150° C. for not more than 25 minutes.

Where propanal is used, the reaction can be represented by the following equation:

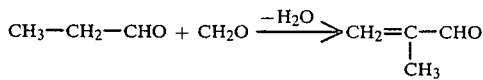

The invention takes into account the fact that not only the yield but also other results of the reaction, some of which are even more important, have to be considered in order to achieve a useful process. Compared with the prior art, the process according to the invention gives a combination of comparatively optimum results, for example high selectively based on both components (alkanal and formaldehyde) at virtually quantitative conversion, high space/time yield, high catalyst performance Q (=moles of α-alkylacrolein-/equivalent of secondary amine), good product quality (directly processible further), low technical complexity and absence of serious toxicity problems. All these results are surprising in view of the conventional processes.

The process is distinguished from the conventional methods particularly surprisingly by an extreme increase in the space/time yields coupled with excellent selectivity. It makes it possible to produce very pure α-alkylacroleins by a technically and economically advantageous procedure, and is therefore, inter alia, very useful for the production of methacrolein, which, even in the form of the crude distillate containing 2-3% of water, is very suitable for the preparation of methacrylic acid by oxidation with $O_2$.

It is surprising that the novel process, where low amounts of amine and substantially shorter reaction times are employed, permits high conversions and, in spite of the use of high temperatures, gives α-alkylacroleins in high yields and almost free of by-products, in a simple reactor, e.g. a tube reactor, without a large excess of formaldehyde or of the appropriate alkanal having to be employed.

Moreover, in view of Russ. Chem. Rev. (loc. cit.), it was not to be expected that virtually no by-products would be formed at above 150° C. According to Kinet, Catal., 4 (1963), 464, polymerization and the formation of by-products take place even under nitrogen and when an inhibitor is used. The processes described in German Laid-Open application DOS No. 2,855,504 and DOS No. 3,025,350, too, are restricted to 70°-120° C., although the lower temperature of 110° C. is given as the upper limit of the preferred temperature range. In U.S. Pat. No. 2,518,416, a yield of only 51% is obtained where the preparation of α-ethylacrolein is carried out at the high temperatures of 200°-220° C. (Example 1).

The alkanal II is reacted with formaldehyde in stoichiometric amounts, or using an excess of one or other of the reactants; as a rule from 0.9 to 1.5, preferably from 0.95 to 1.2, advantageously from 1 to 1.1, in particular 1, mole of starting material II is employed per mole of formaldehyde. The formaldehyde is advantageously used in aqueous solution which is advantageously from 20 to 60% strength by weight.

Preferred starting materials II, and accordingly preferred end products I, are those of the formulae where $R^1$ is n-alkyl of 1 to 8, preferably 1 to 4, carbon atoms. The above radicals can be further substituted by groups which are inert under the reaction conditions, e.g. alkoxy or alkyl of 1 to 4 carbon atoms.

Thus, examples of suitable starting materials II are propanal, n-butanal, 3-methylbutanal, n-pentanal, n-hexanal, 3-methylhexanal, 3-ethylpentanal, 4-methylhexanal, n-heptanal, n-octanal and n-nonanal.

The reaction can be carried out in the absence of acids, but is advantageously carried out in the presence of an acid, as a rule an inorganic acid, or an organic mono-, di- or polycarboxylic acid, preferably a monocarboxylic acid, in particular an aliphatic monocarboxylic acid.

The carboxylic acids used are advantageously aliphatic monocarboxylic acids of 1 to 10, preferably 2 to 4, carbon atoms, dicarboxylic acids of 2 to 10, preferably 2 to 6, carbon atoms of polycarboxylic acids of 2 to 10, preferably 4 to 6, carbon atoms. The dicarboxylic acids and polycarboxylic acids are aromatic, araliphatic or, preferably, aliphatic. Examples of suitable acids are acetic acid, propionic acid, methoxyacetic acid, n-butyric acid, isobutyric acid, oxalic acid, succinic acid, tartaric acid, glutaric acid, adipic acid, maleic acid and fumaric acid. Other organic acids can in principle also be used, but as a rule are more expensive and hence less advantageous.

The inorganic acids employed are as a rule sulfuric acid and phosphoric acid, and mixtures of acids may also be used. From 0 to 0.25, advantageously from 0.01 to 0.1, preferably from 0.02 to 0.05, equivalent of acid is used per mole of alkanal II.

Advantageous amines are those of the formula

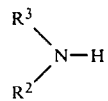 III where $R^2$ and $R^3$ are identical or different and are each alkyl of 1 to 10, advantageously 1 to 8, in particular 1 to 4, carbon atoms, which can be further substituted by ether, hydroxyl, secondary amino or tertiary amino groups, in particular by 1 or 2 of these groups, or are each aralkyl of 7 to 12 carbon atoms or cycloalkyl of 5 to 7 carbon atoms, or $R^2$ and $R^3$, together with the adjacent nitrogen, may furthermore be members of a heterocyclic ring which is advantageously 5-membered to 7-membered, can contain a further nitrogen atom and/or an oxygen atom, and can be substituted by hydroxyalkyl or alkyl, each of 1 to 4 carbon atoms.

Examples of suitable amines III are dimethylamine, diethylamine, methylethylamine, methylpropylamine, dipropylamine, dibutylamine, diisopropylamine, diisobutylamine, methylisopropylamine, methylisobutylamine, methyl-sec.-butylamine, methyl-(2-methylpentyl)-amine, methyl-(2-ethylhexyl)-amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine and dicyclohexylamine, as well as mixtures of these.

From 0.001 to 0.25, advantageously from 0.01 to 0.1, preferably from 0.02 to 0.05, equivalent of amine is used per mole of alkanal II.

The ratio of the number of equivalents of amine to that of the acid is preferably chosen such that the resulting pH is from 2.5 to 7. The reaction is always carried out at above 150° C., advantageously from 150° to 300° C., preferably from 160° to 220° C., in particular from 160° to 210° C., and always under superatmospheric pressure, either batchwise or, advantageously, continuously. The reaction pressure is above 1 bar, as a rule from 1 to 300, expediently from 5 to 300, advantageously from 10 to 150, preferably from 20 to 100, in particular from 40 to 80, bar. The pressure and temperature are set so that the reaction always takes place at below the boiling point of the reaction mixture.

The residence time or reaction time is not more than 25, expediently from 0.01 to 25, advantageously from 0.015 to 10, preferably from 0.03 to 1, in particular from 0.05 to 0.5, particularly preferably from 0.05 to 0.3, minutes. Where the residence time is less than 10 minutes, a tube reactor is advantageously employed.

The reaction mixture can contain water as well as organic solvents, e.g. propanol, dioxane, tetrahydrofuran or methoxyethanol.

The reaction can be carried out as follows: a mixture of starting material II, amine III, formaldehyde and advantageously water and/or an acid is kept at the reaction temperature and the reaction pressure for the reaction time.

In a preferred embodiment a mixture (advantageously one containing equimolar amounts) of formaldehyde and starting material II is heated to the desired reaction temperature by means of a heat exchanger and then fed to a tube reactor. A catalyst solution, i.e. a solution of the secondary amine and an acid, advantageously in $H_2O$, is, if appropriate, likewise heated to the reaction temperature by means of a heat exchanger, and is sprayed into the above mixture, at the entrance to the reactor. The highly exothermic reaction takes place, and the reaction mixture becomes hotter. The pressure under which the reaction takes place is kept, by means of a pressure-regulating valve at the reactor exit, at a value such that the reaction mixture still remains liquid during the reaction time, even when the temperature in the reactor is high. After the reaction, the mixture is let down to atmospheric pressure, and is worked up. In the preparation of methacrolein from propanal and formaldehyde, the reaction mixture is preferably fed to a column, where it is stripped with steam. The methacrolein, together with the water, leaves the column at the top, the mixture is condensed, and separated into an upper and a lower phase in a phase-separating vessel, the upper phase, which contains the methacrolein, is collected in a vessel, and the lower phase, which principally comprises water, is recycled to the column to remove any dissolved methacrolein still present in this phase. The aqueous catalyst solution is taken off at the bottom of the column, together with the water formed during the reaction and that initially present in the formaldehyde solution. Where a very small amount of amine has been employed and hence recycling the catalyst is of no value, the bottom liquid can be discarded. However, where the amine concentration in the bottom product is relatively high, water may also be partially distilled off and the catalyst solution recycled to the reactor. Furthermore, the bottom product can be divided into two bleed streams in such a manner that one of these carries exactly that amount of water which corresponds to the amount of water formed during the reaction together with that fed in with the starting materials. This bleed stream is then separated off, and the remaining stream is recycled to the reactor. Aqueous formaldehyde and alkanal II can also be separately preheated and fed to the reactor. Where an alkanal II which is immiscible with aqueous formaldehyde is employed for the reaction, it is advantageous to feed in the reactants separately.

Separating the reaction mixture by distillation of steam distillation in a column is only one of the possible methods of working up, a further possible procedure being, for example, extraction of the end product I from the catalyst solution with a suitable solvent, e.g. 2-ethylhexanol. Where the end product I has a low solubility in the catalyst solution, a simple phase separation procedure may also be adequate.

The α-alkylacroleins obtainable by the process are useful starting materials for dyes, drugs and pesticides. Oxidation of methacrolein gives the corresponding methacrylic acids and methacrylates, which are useful in the production of plastics, acrylic glasses, molding materials, profiles, surface coatings, lubricating oils, adhesives and textile auxiliaries. Regarding the use of the products, reference may be made to the above literature and to Ullmans Encyklopädie der technischen Chemie (4th edition), Volume 16, pages 609–614.

EXAMPLE 1

The reactor used was a tube reactor (4 ml) with a pressure-regulating valve at the end of the tube. The reactor exit was connected to a column, and the pressure-regulating valve was set so that the reaction took place in the liquid phase, under a pressure of 48 bar.

From a vessel, 1,574 ml per hour of a mixture of 661 g of propionaldehyde with a 37% by weight strength solution containing 342 g of formaldehyde (molar ratio 1:1) were pumped into a heat exchanger, heated to 161° C. therein and then fed to the tube reactor. 524 ml/hour of an aqueous catalyst solution, taken from a second vessel and likewise heated to 161° C. in a heat exchanger, was sprayed into the above mixture, at the entrance to the reactor. The catalyst solution contained 3.66% by weight of dimethylamine and 5.27% by weight of acetic acid. These amounts corresponded to 0.037 mole of amine and 0.04 mole of acetic acid, in each case per mole of propionaldehyde employed. The highly exothermic reaction gave rise to an increase in the temperature. During the reaction, temperatures from 161° to 184° C. were measured. The residence time was 6.9 seconds and the pH was 5.6. The pressure of the reaction mixture was then let down, and the mixture was stripped with steam, this operation being carried out in the column. 809.8 g/hour of organic phase containing 96.7% by weight of methacrolein were obtained at the top of the column. This corresponded to a yield of 98.1% of theory (based on propionaldehyde employed) and to a reactor space/time yield of 195.8 kg per liter per hour. In addition to water and methacrolein, the organic phase essentially contained, as organic impurities, 0.46% by weight of unreacted propionaldehyde and 0.29% by weight of dimeric methacrolein. The end product could be processed further without prior purification. 1,316 g/hour of the bottom product from the column were collected in another vessel.

EXAMPLE 2

The reaction was carried out by a procedure similar to that described in Example 1, except for the following changes:

Pressure 50 bar; 600.5 g/hour (8.34 moles/hour) of n-butyraldehyde and 699.7 g/hour of formaldehyde solution (8.63 moles/hour of formaldehyde); 132 ml/hour of catalyst solution containing 26.3% by weight of dimethylamine and 38% by weight of acetic acid); molar ratio of formaldehyde:n-butyraldehyde:-dimethylamine:acetic acid = 1.035:1:0.1:0.1; residence time 10 seconds. n-Butyraldehyde and formaldehyde were heated separately to 170° C. by means of a heat exchanger. The catalyst stream, at 20° C., was fed in at the reactor entrance, where the 3 streams met. During the reaction, temperatures from 170° to 193° C. were measured. 703 g/hour of organic phase containing 95% by weight of 2-ethylacrolein (corresponding to 95.3% of theory, based on n-butyraldehyde employed), were obtained, and the space/time yield was 167 kg per liter per hour. In addition to water and 2-ethylacrolein, the organic phase essentially contained, as organic impurities, 2.3% by weight of butyraldehyde and 0.4% by weight of 2-ethylhexenal. 733 g/hour of bottom product were obtained.

EXAMPLE 3

The reaction was carried out by a procedure similar to that described in Example 1, except for the following changes:

2,888 g/hour of an equimolar mixture (20.59 moles each) of propionaldehyde and formaldehyde solution; 333 g/hour of aqueous catalyst solution containing 10% by weight of dimethylamine and 15.3% by weight of acetic acid; pressure 80 bar; molar ratio of formaldehyde:propionaldehyde:dimethylamine: acetic acid = 1:1:0.036:0.041; preheating temperature (heat exchanger) 162° C. During the reaction, temperatures from 189° to 205° C. were measured. Residence time 6 seconds. 1,452 g/hour of organic phase containing 96.5% by weight of methacrolein; yield 97.2% of theory. The organic phase contained, as organic impurities, less than 0.6% by weight of propionaldehyde and less than 1% by weight of dimeric methacrolein, and could be directly processed further. 1,769 g/hour of bottom product were obtained.

EXAMPLES 4 to 6

The reaction was carried out by a procedure similar to that described in Example 1, except for the following changes:

Residence time 7 seconds; 1,585 g/hour of an equimolar mixture, heated to 160° C., of propionaldehyde and formaldehyde solution (11.3 moles/hour of each aldehyde); 520 ml/hour of an aqueous catalyst solution which had been preheated to 160° C. and contained 0.037 mole, per mole of propionaldehyde, of one of the secondary amines below, in combination with acetic acid; pressure 50 bar; the remaining values are summarized in the Table below.

TABLE

| Example No. | Amine | Moles of amine per mole of propionaldehyde | Moles of acetic acid per mole of propionaldehyde | Temperatures during the reaction °C. | Yield (% of theory) |
|---|---|---|---|---|---|
| 4 | diethylamine | 0.037 | 0.042 | 161–186 | 92.3 |
| 5 | piperazine | 0.037 | 0.063 | 161–188 | 95.8 |
| 6 | di-n-butylamine | 0.037 | 0.052 | 161–186 | 92.7 |

EXAMPLE 7

The reaction was carried out by a procedure similar to that described in Example 1, except for the following changes:

Reactor volume 5.5 ml; 3,480 ml per hour of a mixture of 24.76 moles of propionaldehyde and 24.76 moles of formaldehyde (37 percent strength aqueous solution), and 488 ml per hour of an aqueous catalyst solution containing 15% by weight of dimethylamine and 16% by weight of sulfuric acid; pressure 80 bar; molar ratio of formaldehyde: propionaldehyde:dimethylamine:sulfuric acid = 1:1:0.072:0.035. The aldehyde mixture is preheated to 163° C., and the catalyst solution is preheated to 185° C. During the reaction, temperatures from 182° to 194° C. were measured. 1,729 g/hour of organic phase containing 95.2% by weight of methacrolein; yield 95% of theory; space/time yield 299 kg per liter per hour; residence time 5 seconds.

EXAMPLE 8

The reaction was carried out by a procedure similar to that described in Example 1, except for the following changes:

Reactor volume 5.5 ml; 3,450 ml per hour of a mixture of 24.55 moles of propionaldehyde and 24.55 moles of formaldehyde (37 percent strength aqueous solution), and 320 ml per hour of an aqueous catalyst solution containing 15% by weight of dimethylamine and 15.2% by weight of oxalic acid; pressure 80 bar; molar ratio of formalde hyde:propionaldehyde:dimethylamine:oxalic acid = 1:1: 0.046:0.023. The aldehyde mixture was preheated to 159° C. and the catalyst solution was preheated to 174° C. During the reaction, temperatures from 180° to 191° C. were measured. 1,708 g/hour of organic phase containing 96.4% by weight of methacrolein; yield 95.8% of theory; space/time yield 294 kg per liter per hour; residence time 5.3 seconds.

EXAMPLE 9

The reaction was carried out by a procedure similar to that described in Example 1, except for the following changes:

1,531 ml per hour of a mixture of 10.97 moles of propionaldehyde and 10.97 moles of formaldehyde (37% strength aqueous solution), and 511 ml per hour of an aqueous catalyst solution containing 3.79% by weight of dimethylamine and 6.20% by weight of tartaric acid; pressure 50 bar; molar ratio of formaldehyde:propionaldehyde:dimethylamine:tartaric acid=1:1:0.039:0.019; the aldehyde mixture and the catalyst solution were preheated to 168° C. During the reaction, temperatures from 177° to 197° C. were measured. 763 g/hour of organic phase containing 95% by weight of methacrolein; yield 94.4% of theory; space/-time yield 181 kg per liter per hour. Residence time 7 seconds.

We claim:

1. In a process for the preparation of an α-alkylacrolein of the formula

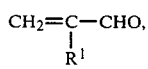

$$CH_2=C-CHO, \quad (I)$$
$$\quad \ \ |$$
$$\quad \ \ R^1$$

where $R^1$ is n-alkyl of 1 to 8 carbon atoms which may be further substituted by alkoxy or alkyle of 1 to 4 carbon atoms, by reacting an alkanal of the formula

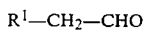

$$R^1-CH_2-CHO \quad (II),$$

where $R^1$ has the above meanings, with formaldehyde in the presence of a secondary amine in the presence or absence of an acid, at from 150° to 300° C., the improvement which comprises carrying out the reaction in the liquid phase under superatmospheric pressure at above 150° C. for not more than 25 minutes, using from 0.001 to 0.25 equivalent of amine per mole of alkanal II.

2. A process as claimed in claim 1, wherein the reaction is carried out using from 0.9 to 1.5 moles of starting material II per mole of formaldehyde.

3. A process as claimed in claim 1, wherein the reaction is carried out using an amine of the formula

where $R^2$ and $R^3$ ar identical or different and are each alkyl of 1 to 10 carbon atoms, which can be further substituted by ether, hydroxyl, secondary amino or tertiary amino groups, or are each aralkyl of 7 to 12 carbon atoms or cycloalkyl of 5 to 7 carbon atoms, or $R^2$ and $R^3$, together with the adjacent nitrogen, may furthermore be members of a heterocyclic ring which is advantageously 5-membered to 7-membered, can contain a further nitrogen atom and/or an oxygen atom, and can be substituted by hydroxyalkyl or alkyl, each of 1 to 4 carbon atoms.

4. A process as claimed in claim 1, wherein the reaction is carried out at from 150° to 300° C.

5. A process as claimed in claim 1, wherein the reaction is carried out at from 160° to 220° C.

6. A process as claimed in claim 1, wherein the reaction is carried out at from 160° to 210° C.

7. A process as claimed in claim 1, wherein the reaction is carried out under a pressure of from 1 to 300 bar.

8. A process as claimed in claim 1, wherein the reaction is carried out for from 0.01 to 25 minutes.

9. A process as claimed in claim 1, wherein the reaction is carried out for from 0.015 to 10 minutes.

10. A process as claimed in claim 1, wherein the reaction is carried out using from 0 to 0.25 equivalent of an acid per mole of alkanal 11.

* * * * *